US006403704B1

(12) United States Patent
Bara

(10) Patent No.: US 6,403,704 B1
(45) Date of Patent: Jun. 11, 2002

(54) COMPOSITION COMPRISING PARTICLES OF A HYDROPHILIC POLYORGANOSILOXANE SUSPENDED IN AN AQUEOUS PHASE

(75) Inventor: Isabelle Bara, Paris (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/500,085

(22) Filed: Feb. 8, 2000

(30) Foreign Application Priority Data

Feb. 8, 1999 (FR) .............................. 99 01447

(51) Int. Cl.$^7$ .................. C08L 83/04; C08G 77/04; A61K 7/02
(52) U.S. Cl. .................. 524/837; 524/860; 524/861; 524/862; 528/15; 528/31; 528/32; 525/474; 525/478; 514/844; 514/845; 514/846; 514/937; 424/401
(58) Field of Search ................. 524/837, 860, 524/861, 862, 27, 702, 732, 763; 528/15, 31, 32; 525/474, 478; 514/844, 845, 846, 937; 424/401

(56) References Cited

U.S. PATENT DOCUMENTS

| 4,761,454 | A | * | 8/1988 | Oba et al. ............... 524/862 |
| 5,169,919 | A | * | 12/1992 | Terae et al. .............. 528/15 |
| 5,412,004 | A |  | 5/1995 | Tachibana et al. |
| 5,599,533 | A |  | 2/1997 | Stepniewski et al. |
| 5,616,598 | A |  | 4/1997 | Lion et al. |
| 5,777,026 | A | * | 7/1998 | Berg et al. ............... 524/837 |
| 5,871,761 | A | * | 2/1999 | Kuwata et al. ............ 424/401 |
| 5,928,660 | A | * | 7/1999 | Kobayashi et al. ........ 424/401 |
| 6,171,581 | B1 | * | 1/2001 | Joshi et al. .............. 424/65 |
| 6,294,608 | B1 | * | 9/2001 | Hager et al. .............. 524/838 |

FOREIGN PATENT DOCUMENTS

| EP | 0 667 146 | 8/1995 |
| EP | 0 687 461 | 12/1995 |
| EP | 0 790 055 | 8/1997 |
| EP | 0 855 178 | 7/1998 |
| JP | 2-295912 | 12/1990 |
| WO | WO 96/36323 | 11/1996 |

OTHER PUBLICATIONS

Patent Abstracts of Japan, vol. 1998, No. 11, Jun. 30, 1998 (JP 10 175816).
Patent Abstracts of Japan, vol. 1997, No. 07, Mar. 3, 1997 (JP 09 067233).
Derwent Publications Ltd., London, GB, Class A26, AN 1995–308979 (XP002120213).
English language Derwent Abstract of EP 0 667 146.
English language Derwent Abstract of EP 0 790 055.
English language Derwent Abstract of JP 2–295912.

* cited by examiner

Primary Examiner—Robert Dawson
Assistant Examiner—Jeffrey B. Robertson
(74) Attorney, Agent, or Firm—Finnegan, Henderson, Farabow, Garrett & Dunner, L.L.P.

(57) ABSTRACT

The invention relates to a composition for cosmetic or topical application comprising particles of an at least partially crosslinked elastomeric solid polyorganosiloxane suspended in an aqueous phase, wherein the composition is substantially water-resistant. This composition is more especially a make-up composition or a care composition for the lips or a foundation composition for making up the human face or body. This composition is soft and feels fresh when applied, it spreads easily, it is non-sticky and it does not dry out the skin or the lips. It is entirely suitable for greasy skin, on account of its high matte-effect power.

18 Claims, No Drawings

COMPOSITION COMPRISING PARTICLES OF A HYDROPHILIC POLYORGANOSILOXANE SUSPENDED IN AN AQUEOUS PHASE

The present invention relates to a care composition and/or a make-up composition for the skin and/or lips of human beings which has not only matte-effect and freshness properties, but also water-resistance properties. Such compositions may be in the form of a lip composition, an eyeliner, a face powder, an eye-shadow, a foundation, an anti-sun product, a deodorant, or a treatment shampoo, in the form of an aqueous gel, a lotion or a cream, or cast as a stick or as a dish.

The known lip and foundation compositions generally comprise fatty substances such as oils, pasty compounds and waxes, as well as a particulate phase generally composed of fillers and pigments. The fillers generally serve to modify the texture of the composition, as well as to give a matte-effect to the film or coat of composition applied to the skin and/or the lips, while the pigments generally serve to bring color to the composition.

A matte-effect is particularly desired for users with combination or greasy skin, as well for use in hot and humid climates. Matte-effect fillers are usually absorbent fillers such as talc, silica, kaolin or fillers which have optical properties of scattering light, these properties being known as the "soft focus" effect.

As taught in European patent application no. EP-A-790 055, matte-effect polymers, such as crosslinked silicone polymers known under the commercial references KSG (KSG 6, 16, 17 and 18) from the company Shin Etsu, Trefils from the company Dow Corning, or Gransils from the company Grand Industrie, have recently been used is cosmetic compositions.

The drawback with these commercial products is that they contain linear or cyclic silicone oils of the non-crosslinked polydimethylsiloxane (PDMS) type, which give an oily, greasy effect and do not feel fresh. Accordingly, it is difficult or impossible to use the resulting products in a hot and humid environment and/or by users with greasy skin. Furthermore, these commercial products, even those which are free of silicone oil (Trefils 505 C from Dow Corning, for example) are difficult to disperse in an aqueous medium. On account of their high incompatibility with water, these polymers have excellent properties of water-resistance or water-remanence, and are presented as "water-insoluble" elastomeric silicone polymers. See, for example, European patent application no. EP-A-0 855 178. Such properties allow elastomeric silicone polymers to be used in so-called "waterproof" compositions, in particular waterproof mascara, eye-liner or anti-sun compositions, the latter being particularly sought after by consumers on holiday by the sea or next to a body of water.

However, the matte-effect power of these polymers has a tendency to fade away over time, once again leading to shiny and greasy effects on the skin, which are aesthetically unattractive. As taught in U.S. Pat. No. 5,412,004 to Kose and U.S. Pat. No. 5,599,533 to Estée Lauder, in order to improve their cosmetic properties, emulsions have recently been formulated containing this type of polymer. Although they have a more fresh and less greasy effect than anhydrous products, these stable emulsions lose their matte-effect property initially provided by the crosslinked silicone polymers.

Compounds of the crosslinked organosiloxane type which can be dispersed in aqueous medium exist. For example, KSG 20 or KSG 21 sold by the company Shin Etsu, exhibit a specific chemical structure that allows it to be dispersed in an aqueous medium. Specifically, the presence of polar groups give the resulting compounds surfactant properties. However, these compounds, unlike those of the composition of the invention, do not provide any particular matte-effect or freshness.

Moreover, the company Procter & Gamble has envisaged, in its International patent application no. WO-A-96/36323, mascara compositions of the water-in-oil emulsion type which are long-lasting, show water resistance and leave no traces. These compositions contain, inter alia, an aqueous polymer dispersion, generally known as a latex, combined with a surfactant of the alkyl or alkoxy dimethicone copolyol type, hydrocarbon-based oils, pigments and fillers, as well as waxes. However, these mascara compositions are unsuitable for use on the skin, because after the water has evaporated, they form a continuous film on the skin which leads to tautness and discomfort, particularly dryness.

The need thus remains for a water-resistant matte-effect composition whose properties persist on the skin over time and which at the same time provide freshness and comfort.

The Inventor has surprisingly discovered that the introduction of particles of a specific polyorganosiloxane into a composition for topical application, and more especially a care composition or a make-up composition for the skin or the lips, makes it possible to overcome the above-described drawbacks. Specifically, the inventive compositions make it possible to obtain a water-resistant film whose cosmetic properties are better than those of the water-resistant products of the prior art. In particular, the present invention provides a water-resistant film that exhibits properties that are superior to those of the prior art, e.g., improved properties related to ease of application, e.g., slipperiness, tautness, dryness, specifically on the lips, freshness, as well as the ability to provide a matte effect.

The invention applies not only to make-up products for the lips and skin of human beings, but also to care products and/or treatment products for human lips and skin. The composition of the invention can also be in the form of a topical composition, which can be applied to the scalp, i.e., areas of superficial keratinous growths, for example.

Thus, one object of the present invention is a composition for cosmetic or topical application comprising particles of an at least partially crosslinked elastomeric solid polyorganosiloxane suspended in an aqueous phase that exhibits improved water-resistance.

Still another object of the present invention is a composition for cosmetic or topical application comprising particles of an at least partially crosslinked elastomeric solid polyorganosiloxane suspended in an aqueous phase that provides a water-resistant make-up or care composition for keratin substances.

Another object of the invention is a process for increasing the water-remanence of a cosmetic composition, which comprises introducing into the composition, by mixing, for example, particles of an at least partially crosslinked elastomeric polyorganosiloxane suspended in an aqueous phase.

It is entirely surprising that the composition is water-resistant although it comprises a continuous aqueous phase. At the present time, no commercially available water-resistant cosmetic product exists which has a continuous aqueous phase.

The term "elastomeric" means a flexible, deformable material which has viscoelastic properties and in particular the consistency of a sponge or a flexible sphere. Its modulus of elasticity is such that this material withstands deformation and has a limited capacity for stretching and contracting. This material is capable of regaining its original shape after it has been stretched. This elastomer is formed from high molecular weight polymer chains whose mobility is limited by a uniform network of crosslinking points.

The elastomeric polyorganosiloxanes of the composition of the invention have properties of structuring an aqueous medium and are capable of increasing the viscosity of the aqueous phase. They do not dry out the skin and provide good cosmetic properties, in particular softness, freshness and a matte effect. These novel elastomers lead to compositions which feel comfortable when applied, spread well, and feel soft and non-sticky to the touch. These cosmetic properties are due both to the texture of the polyorganosiloxanes and to their properties which are comparable to those of microsponges, which trap aqueous media, particularly those of the composition and those due to the perspiration of the skin. They thus make it possible to obtain thickened compositions which have good water-remanence. In addition to the above advantages, the compositions of the invention have good stability.

The compositions of the invention can be in the form of a paste, a solid or a more or less fluid cream. They can be oil-in-water or water-in-oil emulsions which are a fluid, solid or soft hydrophilic gel. The compositions can have the appearance of a lotion, gel, cream or cast product, and can even be in the form of an aerosol.

The elastomeric polyorganosiloxanes in accordance with the invention are partially or totally crosslinked hydrophilic compounds of three-dimensional structure. The thickening of the aqueous phase with these elastomers can be total or partial. It is entirely surprising that hydrophilic polymers have water-remanence properties.

The elastomers of the invention are in the form of a powder or an emulsified gel containing an elastomeric polyorganosiloxane of three-dimensional structure, dispersed in water. The particle dispersion or suspension is homogeneous.

The elastomeric polyorganosiloxanes of the present invention can be chosen from the crosslinked polymers described in Japanese patent application no. JP-A-10/175816, the disclosure of which is incorporated herein in its entirety. According to this Japanese application, elastomeric polyorganosiloxanes are obtained by an addition and crosslinking reaction, in the presence of a catalyst, in particular of the platinum type, of:

(a) at least one polyorganosiloxane (i) with α-ω positions in the silicone chain, having at least two vinyl groups in the α-ω positions of the silicone chain per molecule; and (b) at least one organosiloxane (ii) containing at least one hydrogen atom linked to a silicon atom per molecule.

In particular, the polyorganosiloxane (i) is chosen from polydimethylsiloxanes, and is more specifically an α,ω-dimethylvinylpolydimethylsiloxane. It is understood that while one vinyl group in each of the α and ω positions of the silicone chain per molecule imparts the desired properties, preferably, a polyorganosiloxane having at least two vinyl groups in the α-ω positions of the silicone chain per molecule is used.

The elastomeric polyorganosiloxanes of the composition according to the invention are advantageously in the form of an aqueous suspension. This suspension can be obtained in particular as follows:

(a) mixing the polyorganosiloxane (i) and the organosiloxane (ii);

(b) adding the aqueous phase containing an emulsifier to the mixture of (a);

(c) emulsifying the aqueous phase and the mixture;

(d) adding water to the emulsion of (c); and (e) polymerizing the polyorganosiloxane (i) and the organosiloxane (ii) as an emulsion in the presence of a platinum catalyst.

The water is advantageously added at a temperature above room temperature, preferably 40–60° C. After polymerization, it is possible to dry the particles obtained in order to evaporate therefrom all or some of the trapped water.

The polyorganosiloxanes are in the form of hydrophilic deformable solid particles which have a certain hardness, measurable with a Shore A durometer (according to ASTM standard D2240) at room temperature or by the Japanese method JIS-A. This hardness can be measured on a block of elastomer prepared for this purpose as follows: mixing the polyorganosiloxane (i) and the organosiloxane (ii); removing air from the mixture; molding and vulcanizing in an oven at 100° C. for 30 minutes; cooling to room temperature and then measuring the hardness. The density can also be determined on this block of elastomer.

The Shore hardness is less than or equal to 80, and preferably less than 65. The polyorganosiloxanes of the composition of the invention are, for example, those sold under the names BY 29-122 and BY 29-119 by the company Dow-Corning Electric. A mixture of these commercial products can also be used. A block of elastomers according to the product comprising BY-29-122 has a hardness of 7, and according to the product comprising BY-29-119 has a hardness of 30. The density of these products is typically 0.97 to 0.98.

The elastomeric polyorganosiloxane powder, which acts as a water-dispersible filler, is present in the composition in an amount of from 1 to 99%, and preferably in an amount of from 5 to 70%. The above amounts correspond to an active material content of the polymer of from 0.5 to 65% by weight, and preferably of from 3 to 45%, respectively.

The elastomeric polyorganosiloxane particles, as active material, have a size ranging from 0.1 to 500 µm, and preferably from 3 to 200 µm. While these particles can be flat or amorphous, they preferably have a spherical shape.

In order to disperse stably in water, these polyorganosiloxane particles can be combined with one or more nonionic, cationic or anionic surfactants with a hydrophilic-lipophilic balance (HLB)≧8.

As taught in the description of Japanese patent application no. JP-A-10/175816, the proportion of surfactants is preferably from 0.1 to 20 parts by weight per 100 parts by weight of the elastomeric polyorganosiloxane composition, and more preferably from 0.5 to 10 parts by weight.

These elastomeric polyorganosiloxane powders can be combined with fatty substances that are liquid at room temperature, known as oils, such as those described in Japanese patent application no. JP-A-10/175816, waxes or gums that are solid at room temperature, pasty fatty substances of animal, plant, mineral or synthetic origin, mixtures thereof and inorganic powders such as those described in the above Japanese patent application.

The additional fatty phase can be any fatty phase and can contain products that are fluid at room temperature, such as silicone oils, fluoro oils, fluorosilicone oils and hydrocarbon-based oils which are optionally partially silicone-containing. These oils can be volatile at room temperature and atmospheric pressure. The expression "volatile oil" in particular means an oil which can evaporate in less than one hour when placed in contact with the skin or the lips. These oils can represent from 0 to 80% of the total weight of the composition.

As oils which can be used in the composition of the invention, mention may be made in particular of:

- hydrocarbon-based oils of animal origin, such as perhydrosqualene;
- hydrocarbon-based plant oils, such as liquid fatty acid triglycerides, for example sunflower oil, corn oil, soybean oil, marrow oil, grape seed oil, sesame oil, hazelnut oil, apricot oil, macadamia oil, castor oil, avocado oil, caprylic /capric acid triglycerides such as those sold by the company Stearineries Dubois or those sold under the names Miglyol 810, 812 and 818 by the company Dynamit Nobel;
- oils of formula $R^1COOR^2$ in which $R^1$ represents a higher fatty acid residue comprising from 7 to 19 carbon atoms and $R^2$ represents a branched hydrocarbon-based chain containing from 3 to 20 carbon atoms, such as, for example, purcellin oil;
- linear or branched hydrocarbons of mineral or synthetic origin, such as volatile or non-volatile liquid paraffins and derivatives thereof, petroleum jelly, polydecenes, and hydrogenated polyisobutene such as parleam;
- synthetic esters and ethers, such as isopropyl myristate and alkyl or polyalkyl octanoates, decanoates and ricinoleates;
- fatty alcohols, such as octyldodecanol and oleyl alcohol;
- partially hydocarbon-based and/or silicone-based fluoro oils, such as those described in Japanese patent application no. JP-A-2 295 912, the disclosure of which is incorporated herein in its entirety;
- silicone oils, such as polymethylsiloxanes containing a linear or cyclic silicone chain, which are liquid or pasty at room temperature, phenyl dimethicones, phenyl trimethicones and polymethylphenylsiloxanes;
- mixtures thereof.

Advantageously, the compositions according to the invention can contain hydrocarbon-based waxes, fluoro waxes or silicone waxes or mixtures thereof, which may be solid or semi-solid (in the form of a paste) at room temperature. These waxes may be of plant, mineral, animal and/or synthetic origin. In particular, these waxes have a melting point of greater than 25° C., and preferably greater than 45° C.

The silicone waxes can be waxes comprising a silicone structure and units containing one or more alkyl or alkoxy chains pendant and/or at the end of the silicone structure, these chains being linear or branched and comprising from 10 to 45 carbon atoms. These waxes are referred to respectively as alkyldimethicones and alkoxydimethicones. Moreover, these alkyl chains can comprise one or more ester functions.

As other waxes which can be used in the invention, mention may be made of waxes of animal origin, such as lanolin or beeswax; waxes of plant origin, such as carnauba wax or candelilla wax; waxes of mineral origin, for example, paraffin wax, lignite wax or microcrystalline waxes, ceresine or ozokerite; synthetic waxes, such as polyethylene waxes; and mixtures thereof.

These fatty substances can be chosen in a varied manner by a person skilled in the art in order to prepare a composition which has the desired properties, for example, in terms of consistency or texture.

In particular, the presence of waxes makes it possible to provide good mechanical strength, in particular when the composition is in the form of a stick.

In general, the composition can comprise from 0 to 50% of wax relative to the total weight of the composition, and preferably from 10 to 30%.

The composition of the invention can also comprise at least one additional ingredient usually used in the field concerned, chosen from antioxidants, essential oils, preserving agents, cosmetic or dermatological active agents such as moisturizers (glycerol), vitamins, essential fatty acids and lypophilic sunscreens, lyposoluble polymers, in particular hydrocarbon-based polymers such as polyalkylenes, aqueous-phase gelling agents, fatty-phase gelling agents, fragrances, surfactants, and mixtures thereof.

These additional ingredients can be present in the composition according to the invention in the amounts usually used. For example, additional ingredients can be found in a proportion of from 0 to 20% relative to the total weight of the composition, and preferably from 0.1 to 10%.

Advantageously, the compositions of the invention contain, as an additional ingredient, one or more aqueous-phase gelling agents. Among the aqueous-phase gelling agents which can be used according to the invention, mention may be made of: water-soluble cellulosic gelling agents such a hydroxyethylcellulose, methylcellulose, hydroxypropylcellulose and carboxymethylcellulose; guar gum; quaternized guar gum; nonionic guar gums comprising $C_1$–$C_6$ hydroxyalkyl groups; xanthan gum, carob gum, scleroglucan gum, gellan, rhamsan gum and karaya gum; alginates, maltodextrin, starch and its derivatives; hyaluronic acid and its salts; clays, in particular montmorillonites, hectorites or bentonites, and laponites; polymers containing a carboxylic group, such as at least partially neutralized crosslinked polyacrylic acids, for instance the "Carbopols" or "Carbomers" from the company Goodrich, e.g., Carbomer 980 neutralized with triethanolamine-abbreviated to TEA; polyglyceryl (meth)acrylate polymers; polyvinylpyrrolidone; polyvinyl alcohol; crosslinked acrylamide polymers and copolymers; crosslinked methacryloyloxyethyltrimethylammonium chloride homopolymers; associative polyurethanes; and mixtures thereof.

According to the invention, the aqueous-phase gelling agent is preferably chosen from xanthan gum, clays (bentonite or laponite), associative polyurethanes, cellulosic thickeners, in particular hydroxyethylcellulose, and at least partially neutralized crosslinked polyacrylic acids.

It would be readily apparent to a person skilled in the art to select the optional additional ingredients and/or the amount thereof such that the advantageous properties of the composition according to the invention are not, or are not substantially, adversely affected by the addition envisaged. In particular, these additives must not harm the homogeneity, stability, comfort, matte-effect, freshness or water-resistance of the composition.

The composition according to the invention can be in the form of a colored product and especially a make-up product for the skin, in particular a foundation, a face powder, an eye-shadow, a mascara, an eye-liner, a concealer stick, a nail varnish or a make-up product for the lips, such as a lipstick. They can also be in non-colored form, optionally containing cosmetic or dermatological active agents. In this case, they can be used as a care base for the lips (lip balms for protecting the lips against the cold and/or the sun and/or the wind) or a fixing base to be applied over a conventional lipstick.

The composition of the invention can also be in the form of a dermatological or cosmetic composition for treating or caring for the skin (including the scalp), keratin fibres (hair, eyelashes, eyebrows), the nails or the lips, or in the form of an anti-sun or artificial tanning composition, or alternatively in the form of a cleansing product or a product for removing make-up from the skin or keratin fibres, a deodorant product or a fragrancing product.

The composition of the invention should be cosmetically and dermatologically acceptable, i.e. non-toxic, and able to be applied to the skin, including the inside of the eyelids, or to the lips of human beings.

Preferably, the composition of the invention can comprise a dyestuff, particularly containing a particulate phase. Generally, a dyestuff can be present in a proportion of from 0 to 60% relative to the total weight of the composition, more preferably of from greater than 0.1 to 60% relative to the total weight of the composition, and still more preferably from 5 to 35%. The dyestuff can comprise pigments and/or nacres and/or fillers usually used in cosmetic compositions. Alternatively, dyes which are soluble in the medium, and in particular water-soluble or liposoluble dyes can be used.

The term "pigments" should be understood to mean white or colored, inorganic or organic particles which are insoluble in the medium of the composition and are intended to color and/or opacify the composition. The term "fillers" should be understood to mean colorless or white, inorganic or synthetic, lamellar or non-lamellar particles. The term "nacres" should be understood to mean iridescent particles, produced in particular by certain mollusks in their shell, or else synthesized. These fillers and nacres serve to modify the texture of the composition as well as the matte-effect/gloss.

The pigments can be present in the composition in a proportion of from 0 to 60% relative to the weight of the final composition, and preferably in a proportion of from 4 to 25%. As inorganic pigments which can be used in the invention, mention may be made of titanium oxide, zirconium oxide or cerium oxide, as well as zinc oxide, iron oxide or chromium oxide and ferric blue. Among the organic pigments which can be used in the invention, mention may be made of carbon black and barium, strontium, calcium and aluminium lakes, and mixtures thereof.

The nacres can be present in the composition in a proportion of from 0 to 20% relative to the total weight of the composition, and preferably in a proportion from about 2 to 15%. Among the nacres which can be used in the invention, mention may be made of mica coated with titanium oxide, with iron oxide, with natural pigment or with bismuth oxychloride, such as colored titanium mica.

The fillers can be present in a proportion of from 0 to 35% relative to the total weight of the composition, and preferably from 5 to 15%. Mention may be made in particular of talc, mica, silica, Nylon® powder (Orgasol® in particular from Atochem) and polyethylene powder, Teflon®, starch, boron nitride, and silicone resin microbeads (Tospearl® from Toshiba, for example), and mixtures thereof.

The water-soluble dyes are, in particular, beetroot juice or methylene blue and can represent from 0 to 6% relative to the total weight of the composition.

The composition according to the invention can be manufactured without heating or by heating one or more elastomeric polyorganosiloxanes in the form of a powder dispersed in water, adding one or more pigments, one or more fillers and/or one or more other additives, optionally adding the fatty phase in liquid form (in particular brought to the highest melting point of the waxes), followed by emulsification, if necessary.

The composition can also be obtained by extrusion as described in European patent application no. EP-A-667 146, the disclosure of which is incorporated by reference herein in its entirety. This process consists in blending the paste (waxes +oils +additives +pigments) during the cooling in order to create, in the bulk zones for crushing, a paste with the aid of a roll mill or a screw extruder-mixer. This process makes it possible to obtain a composition in the form of a soft paste.

The invention is illustrated in greater detail in the examples which follow. The percentages are given on a weight basis.

EXAMPLE 1

Preparation of an Anti-sun Gel

| | |
|---|---|
| Carbomer 980 | 0.3% |
| TEA | 3% |
| Silicone BY 29-119 | 15% |
| Hydrophilic treated nanometric TiO$_2$ | 3% |
| Mexoryl SX (*) | 0.5% AM |
| Preserving agent | qs |
| Water | qs 100% |

(*) benzene-1,4-bis(3-methylidene-10-camphorsulphonic acid) which is a hydrophilic broad-band ultraviolet screening agent.

Result

A composition according to this example resulted in a gel with a pronounced matte effect, which felt very fresh when applied, had good staying power over time, and had good water-resistance, unlike the products of the prior art.

Preparation

The polyorganosiloxane was added to the water at room temperature, followed by addition of the gelling agent, the neutralizing agent, the TiO$_2$, the Mexoryl SX and the preserving agents. The combination of components was then mixed together with stirring.

EXAMPLE 2

Preparation of a Water-resistant, Fresh-feeling Matte Foundation

Silicone BY 29-122 70%

Pigments (iron oxides) 7%

Talc 10%

Glycerin 5%

Preserving agent qs

Water qs 100%

Result

A composition according to this example resulted in a foundation which felt fresh, had a pronounced matte effect, good staying power over time and good water-resistance.

Preparation

This composition was prepared as in Example 1.

A comparative test of water-resistance was carried out on an eye-shadow with a continuous aqueous phase, containing or not containing the hydrophilic crosslinked polyorganosiloxane. The water-resistance was measured on a film 50, 100, 150 and 300 µm thick deposited on a glass plate which was left to dry at room temperature for one hour. A trickle of water was allowed to flow continuously and the time required for the film to begin to degrade was measured.

Example 3

Preparation of An Eye-shadow Containing a Hydrophilic Polyorganosiloxane

| | | | | |
|---|---|---|---|---|
| Trefil BY 29-119 | | 32% | | |
| Carbopol 980 | | 0.58% | | |
| TEA | | 0.58% | | |
| Brown nacre | | 5% | | |
| Talc | | 5% | | |
| Preserving agent | | 0.75% | | |
| Water | | qs 100% | | |
| Thickness of the drawn film ($\mu$m) | 50 | 100 | 150 | 300 |
| Time (sec)* | 10 | 20 | 22 | 35 |

*Water-resistance (after drying for 1 h)

COMPARATIVE EXAMPLE

Preparation of an Eye-shadow not Containing a Hydrophilic Crosslinked Polyorganosiloxane

| | | | | |
|---|---|---|---|---|
| Carbopol 980 | | 0.58% | | |
| TEA | | 0.58% | | |
| Brown nacre | | 5% | | |
| Talc | | 5% | | |
| Preserving agent | | 0.75% | | |
| Water | | qs 100% | | |
| Thickness of the drawn film ($\mu$m) | 50 | 100 | 150 | 300 |
| Time (sec)** | 2 | 8 | 15 | 20 |

**Water-resistance (after drying for 1 h)

The eye-shadow according to the invention felt remarkably fresh, soft and smooth and had noteworthy water-resistance. According to the test, it was found that the time required to degrade the film in the presence of water was greater for the composition containing the polyorganosiloxane than for the composition not containing a polyorganosiloxane.

What is claimed is:

1. A method for increasing the water-resistance of a composition, wherein said method comprises introducing into said composition particles of an at least partially crosslinked elastomeric polyorganosiloxane suspended in an aqueous phase.

2. The method according to claim 1, wherein said elastomeric polyorganosiloxane is obtained by an addition and crosslinking reaction, in the presence of a catalyst, of:
   at least one polyorganosiloxane (i) with $\alpha$-and $\omega$-positions in the silicone chain, having at least two vinyl groups in the $\alpha$-and the $\omega$-positions of the silicone chain per molecule; and
   at least one organosiloxane (ii) containing at least one hydrogen atom linked to a silicon atom per molecule.

3. The method according to claim 2, wherein the polyorganosiloxane (i) is a polydimethylsiloxane.

4. The method according to claim 3, wherein the polyorganosiloxane is an $\alpha,\omega$-dimethylvinylpolydimethylsiloxane.

5. The method according to claim 2, wherein a suspension of polyorganosiloxane particles is obtained according to the following:

(a) mixing a polyorganosiloxane (i) and an organosiloxane (ii);
   (b) adding an aqueous phase comprising an emulsifier to the mixture obtained in (a);
   (c) emulsifying the aqueous phase and the mixture to obtain an emulsion;
   (d) adding water to the emulsion of (c); and
   (e) polymerizing the polyorganosiloxane (i) and the organosiloxane (ii) as an emulsion in the presence of a platinum catalyst,
   wherein the temperature of the water added in (d) is above room temperature.

6. The method according to claim 5, wherein said emulsion of (c) is obtained in the presence of a nonionic emulsifier.

7. The method according to claim 1, wherein said particles have a size ranging from 0.1 to 500 $\mu$m.

8. The method according to claim 7, wherein said particles have a size ranging from 3 to 200 $\mu$m.

9. A method according to claim 1, wherein said composition further comprises a fatty phase.

10. A method according to claim 9, wherein said fatty phase contains at least one fatty substance chosen from volatile and non-volatile oils, waxes, gums and pasty fatty substances of animal, plant, mineral and synthetic origin, and mixtures thereof.

11. A method according to claim 1, wherein said composition further comprises an aqueous-phase gelling agent.

12. A method according to claim 11, wherein said aqueous-phase gelling agent is chosen from xanthan gum, clays, associative polyurethanes, cellulosic thickeners and at least partially neutralized crosslinked polyacrylic acids, and mixtures thereof.

13. A method according to claim 1, wherein said composition further comprises a particulate phase present in an amount ranging from greater than 0.1 to 60%, relative to the total weight of the composition.

14. A method according to claim 13, wherein said particulate phase is present in an amount ranging from 5 to 35%, relative to the total weight of the composition.

15. A method according to claim 1, wherein said composition further comprises at least one cosmetic or dermatological active agent.

16. A method according to claim 1, wherein said composition is in the form of a foundation, a face powder, an eye-shadow composition, a concealer product, a lip composition, an eye-liner, a mascara, a nail varnish, a care base or a fixing base for the lips, a dermatological product or a care product for the skin or keratin fibres, an antisun or artificial tanning composition, a cleansing product for the skin or keratin fibres, a deodorant product or a fragrancing product.

17. A method according to claim 1, wherein said composition further comprises at least one dyestuff.

18. A method according to claim 1, wherein said composition further comprises at least one ingredient chosen from preserving agents, antioxidants, fragrances, fatty-phase gelling agents and surfactants, and mixtures thereof.

* * * * *